United States Patent
Takamura et al.

[11] Patent Number: 6,146,514
[45] Date of Patent: Nov. 14, 2000

[54] APPARATUS AND METHOD FOR MEASURING ACIDITY

[75] Inventors: Kiyoko Takamura, Yokohama; Fumiyo Kusu, Hachiouji; Takeshi Nishida, Ogohri; Hideaki Hashimoto, Miyaki-gun; Hidefumi Yabu, Ohnojou; Kazuyoshi Mori, Kasuga; Yuji Hiraishi, Chikushino; Yasuyuki Hanada, Kasuga; Tetsuji Soeda, Kumamoto; Tsuyoshi Kusakabe, Chikushi-gun; Tetsuya Nishio, Fukuoka, all of Japan

[73] Assignee: Matsushita Electric Industrial Co., Ltd., Osaka, Japan

[21] Appl. No.: 09/020,139

[22] Filed: Feb. 6, 1998

[30] Foreign Application Priority Data

Feb. 12, 1997 [JP] Japan .................................... 9-027401
Oct. 8, 1997 [JP] Japan .................................... 9-275499

[51] Int. Cl.[7] .............................. G01F 1/64; G01N 27/26
[52] U.S. Cl. ......................... 205/77.5; 205/792; 204/413; 204/433
[58] Field of Search ................................ 205/775, 787.5, 205/789, 792; 204/405, 416, 433

[56] References Cited

U.S. PATENT DOCUMENTS

| | | |
|---|---|---|
| 3,623,960 | 11/1971 | Williams . |
| 3,674,661 | 7/1972 | Hughes .................................... 204/400 |
| 4,401,548 | 8/1983 | Brezinski ................................ 204/420 |
| 5,037,968 | 8/1991 | Simon et al. . |
| 5,223,117 | 6/1993 | Wrighton et al. ........................ 204/415 |
| 5,239,258 | 8/1993 | Kauffman . |

FOREIGN PATENT DOCUMENTS

| | | |
|---|---|---|
| 0190740 | 8/1986 | European Pat. Off. . |
| 05264503 | 10/1993 | Japan . |
| 5264503 | 10/1993 | Japan . |

OTHER PUBLICATIONS

K. Takamura et al., Japan Analyst, vol. 18, pp. 309–314, 1969.

K. Takamura et al., Proceedings of the Electrochemical Society, pp. 93–11, 443–450, 1993, "Utilization of Electrochemical Reduction of Quinones for Determining Free Fatty Acid Content in Fats and Oils."

F. Kusu et al.; Journal of AOAC International, vol. 77, No. 6, pp. 1686–1689, 1994, "Voltammetric Determination of Acid Values of Fats and Oils."

F. Kusu et al.; ASIC, pp. 351–358, 1995; "Determination of Acid Content in Coffee Beans and Coffee."

Chemical Abstract, 122: 109258d (1995), vol. 122, No. 10, "Voltammetric Determination of Free Fatty Acid Content in Fats and Oils".

Chemical Abstract, 89:99325g (1978), vol. 89, No. 12, "Determination of Organic Acids".

Chemical Abstract, vol. 65, No. 12, (1966) "Polarographic Studies of Oxidation of Ascorbic Acid By Quinones".

Chemical Abstract, 67437m, "Effect of Substituents on the Redox Potential of Substituted 1,4–Benzoquinones" (1969).

Chemical Abstract 92–129744, SU Patent 1649410, "Voltameter Determine High Fatty Unsaturated Acid . . . " (1991).

*Primary Examiner*—Robert J. Warden, Sr.
*Assistant Examiner*—Andrew Aldag
*Attorney, Agent, or Firm*—Renner, Otto, Boisselle & Sklar, LLP

[57] ABSTRACT

An acidity measuring apparatus includes a measuring container for accommodating an electrolyte solution including one of a 1,2-benzoquinone derivative and a 1,4-benzoquinone derivative, an organic solvent, an electrolyte and an acid-containing subject for measurement; a working electrode, a counter electrode and a reference electrode section provided in the measuring container and immersed in the electrolyte solution; and a control section for sweeping a potential of the working electrode within a prescribed range and for detecting a value of a pre-peak current generated by the acid and flowing between the working electrode and the counter electrode.

27 Claims, 11 Drawing Sheets

APPARATUS AND METHOD FOR MEASURING ACIDITY

BACKGROUND OF THE INVENTION

1. Field of the Invention

The present invention relates to an apparatus and method for measuring acidity of free fatty acids contained in oil such as edible oil; citric acid, malic acid or tartaric acid contained in fruit juice or fruit juice drinks; organic acids contained in alcoholic drinks; organic acids such as chlorogenic acids contained in coffee; or free fatty acids released from substrate oil by enzyme reaction of esterase in serum.

2. Description of the Related Art

Recently, it has been demanded that food have a quality above certain criteria for health and safety reasons. Among various components contained in food, acid has a significant influence on the quality of the food. Moreover, food having a relatively low acid content has been preferred recently. Acidity of various types of food has a considerable influence on the quality of food. The degree of influence and the method for measurement of the acidity vary in accordance with different types of food. Hereinafter, conventional methods for measuring the acidity of (1) edible oil, (2) fruit drinks such as juice, (3) alcoholic drinks such as whisky, "sake" or wine, (4) coffee, and (5) juice contained in fruits such as oranges or grapes will be described.

(1) Edible oil:

Diet in Japan is rapidly changing. A first change is the inclination for instant food. A second change is the diversification of tastes, which is represented by the increase in sales of processed food. Specifically, the increased preference for precooked food can be considered as reflecting the times, and a greater variety of processed food are being consumed in greater quantities. Especially, consumption of fried food has shown a remarkable increase. Some of the reasons for this increase are that fried food is preferred in terms of taste and is relatively less perishable. Even in the case of fried food, though, after being left in conditions where the influence of the temperature or light is significant, fats and oils are spontaneously oxidized by oxygen contained in the air, resulting in generation of putrid smell and deterioration of quality. For these reasons, general concern has grown regarding putrefaction and deterioration of edible fats and oils and processed food cooked with oils. For example, a regional food authentification system for fried bean curd has been started or a restriction on fried snacks has been introduced. Legal restriction of deterioration of fats and oils has been discussed in terms of establishing guidelines for boxed lunches and ready-made dishes sold in stores.

In order to examine the degree of deterioration of such fats and oils, especially heated fats and oils, there are several methods available for analysis, e.g., measurement of the acid value, the peroxide value, viscosity, and iodine value. Considering that food deterioration is mostly influenced by the temperature, humidity and light and that the acidity significantly changes during the initial stage of deterioration, measurement of acid value by which the acidity is directly measured, is appropriate and commonly used.

(2) Fruit drinks such as juice:

Fruit juice drinks are obtained by subjecting the fruits to squeezing. More fruit juice drink products are produced from concentrated fruit juice or frozen fruit juice rather than from fresh squeezed fruit juice.

For example, orange juice products are produced by removing blighted and unripe oranges, then washing the peel, pressurizing the oranges to take out the pulp and juice, and removing the pericarp, and the like from the juice. At this point, the sugar concentration, the acidity and the like are adjusted in conformity with the Japanese Agricultural Standards. At this point, the acidity is measured. In the case of producing orange juice from concentrated juice or frozen juice by adding water, the acidity is also measured at the time of adding water.

(3) Alcoholic drinks:

There are various types of alcoholic drinks produced in various manners. For example, distilled liquor represented by whisky or "shochu" is produced by repeating distillation to increase the yield of ethanol. Drinks represented by "sake" or wine are produced by fermentation and filtering. There are still other types of alcoholic drinks, e.g., effervescent liquor such as fruit wine or beer. Either type of alcoholic drink is subjected to acidity measurement during a production process in order to assure the quality.

(4) Coffee:

There are many types of substances as mentioned below providing a sour taste which mainly determines the taste of coffee. The acid content is important as a criterion for evaluating the sour taste of coffee. A representative type of acid contained in coffee is chlorogenic acids. The acid content thereof changes even while the coffee beans are roasted. Other substances such as coffee acid, quinic acid, and citric acid which are associated with the sour taste of coffee. Although the amount of each acid is very small, the delicate balance of the acid combination and the total amount of acid are considered to determine the sour taste in coffee.

(5) Juice contained in fruits such as oranges:

During the cultivation of oranges, especially during cultivation in a greenhouse, drying the inside of the oranges by withholding water is performed in order to increase the sugar level. According to this method, the concentration of sugar and acid in the fruit juice is increased by restricting the amount of water. However, as the sugar level increases in the fruit juice, the pleasant taste is enhanced; whereas as the acidity increases, the taste is worsened. Accordingly, after the inside of the oranges is dried by withholding water, the acid is consumed by causing the oranges to respire using an appropriate amount for water and an appropriate temperature while monitoring the acidity.

As described above, acidity is measured during the production of various types of food. There are a variety of methods available. Conventional acidity measuring methods are defined by, for example, the standard methods for analysis of oils and fats in the Official and Tentative Methods of the American Oil Chemists' Society, the Standard Methods for the Analysis of Oils, Fats and Derivatives of the Japan Oil Chemists' Society, the Japanese Agricultural Standards, the Japanese Industrial Standards, the Test for Fats and Fixed Oils of the Japanese Pharmacopoeia, the Standard Methods of Analysis for Hygienic Chemists, and the Potable Water Test Method. All of these methods are based on a neutralization titration method using phenolphthalein as an indicator. The neutralization titration methods defined in the Potable Water Test Method and the Standard Methods for the Analysis of Oils, Fats and Derivatives of the Japan Oil Chemists' Society will be described.

In the Potable Water Test Method, the acidity is defined as the amount in milligrams of calcium carbonate contained in 1 liter of sample. In practice, the acidity is obtained in the following manner.

One hundred milliliters of sample water is taken. Next, about 0.2 mL of phenolphthalein indicator solution is added to the test water, and then a solution of 0.02 mM sodium hydroxide is added thereto. The container containing the resultant mixture is sealed and lightly shaken. After the pink color disappears, another solution of 0.02 mM sodium hydroxide is added, and the container is sealed and lightly shaken. The titration is continued until the faint but permanent pink color is visually observed even after shaking, and this point is defined as the end point of the neutralization. The volume a of sodium hydroxide in milliliters at the end point is obtained. The acidity is calculated by the formula:

Acidity (mg/L of calcium carbonate)=$a \times 10$

The acidity of the tap water is indicated by the amount of calcium carbonate in milligrams per liter as described above. The acidity of other representative acid-containing substances are indicated as follows.

The acidity of oranges is converted and indicated by the amount in weight percent of citric acid. The acidity of grapes is indicated by the amount in weight percent of tartaric acid. The acidity in fats and oils is, as described in detail below, indicated by an acid value, which is the amount in milligrams of potassium hydroxide required to neutralize the free fatty acid contained in 1 gram of fats and oils. As described above, the indicator representing the acidity is defined for each different type of substances.

The neutralization titration method defined in the Standard Methods for the Analysis of Oils, Fats and Derivatives will be described in the case where it is used to determine the acidity of fats and oils. In the Standard Methods for the Analysis of Oils, Fats and Derivatives, the acid value is defined as the amount in milligrams of potassium hydroxide required to neutralize the free fatty acid contained in 1 gram of fats and oils.

The acidity of a liquid sample is measured in the following manner. An amount of the sample is taken in accordance with an estimated acid value (for example, 20 grams for the estimated acid value of 1 or less, 10 grams for the estimated acid value of more than 1 but equal to or less than 4, and 2.5 grams for the estimated acid value of more than 4 but equal to or less than 15). The accurate intended amount of sample is measured and put into an Erlenmeyer flask. One hundred milliliters of neutral solvent is added, and shaken until the sample is completely dissolved. The neutral solvent herein is obtained by adding about 0.3 mL of phenolphthalein indicator solution to a 1:1 mixed solvent of ethylether and ethanol, and neutralizing the resultant substance by 1/10 N potassium hydroxide-ethanol solution immediately before use.

The acidity of a solid sample is measured in the following manner. The sample is melted by heat in a water bath. Then, a solvent is added and the sample is dissolved. The resultant substance is titrated by 1/10 N potassium hydroxide-ethanol standard solution, and the time when the pink color of the indicator continues for 30 seconds is defined as the end point of neutralization. The amount in milligrams of potassium hydroxide is obtained by calculation.

The acid value of the fats and oils such as edible oil can be obtained through the measurement of the fatty acid by voltammetry rather than the neutralization titration. According to this method, which is disclosed in Japanese Laid-Open Publication No. 5-264503, the amount of the fatty acid in the electrolyte solution containing both free fatty acid and a naphthoquinone derivative is measured by voltammetry at a controlled potential. This method utilizes the property that the current value of the pre-peak of voltammetric reduction of the naphthoquinone derivative changes in proportion to the concentration of all types of free fatty acid, including lower fatty acid such as formic acid and higher fatty acid such as oleic acid and linoleic acid, and that the value obtained by overlapping the current values of different types of fatty acids corresponds to the total concentration of the fatty acids. In other words, the acid concentration is measured by measuring the current value of the pre-peak of voltammetric reduction of the naphthoquinone derivative. FIG. 17 is a graph illustrating the current vs. potential relationship for acidity measurement by voltammetry of an electrolyte solution containing a naphthoquinone derivative. The solid line in FIG. 17 indicates the data obtained by such a method of measurement. In FIG. 17, the axis of abscissa represents the potential of a working electrode with respect to the potential of a reference electrode in the case where the reference electrode is formed of silver—silver chloride and the working electrode is formed of $\phi 3$ glassy carbon. The axis of ordinates represents the value of the current flowing in the circuit. It should be noted that the current value varies in accordance with various conditions such as the surface area of the working electrode while the current value slightly fluctuates in accordance with the acid concentration; the fluctuation is negligible. In FIG. 17, letter A indicates the pre-peak depending on the acid concentration, and letter C indicates the main peak of the naphthoquinone derivative.

In order to measure the acid value of fats and oils by the method disclosed in Japanese Laid-Open Publication No. 5-264503, nitrogen gas or the like needs to be supplied to the electrolyte solution so as to remove the oxygen dissolved in the electrolyte solution. The data represented by the solid line in FIG. 17 is obtained in the state where the dissolved oxygen is removed. Unless the dissolved oxygen is removed, the current for reducing the dissolved oxygen flows and thus it becomes difficult to determine the current value of the pre-peak of reduction. The dotted line in FIG. 17 represents the reduction curve in the case where the dissolved oxygen is not removed. As can be seen in FIG. 17, the reduction curve of the oxygen and the pre-reduction curve overlap and thus the pre-peak of the fatty acid can hardly be determined. The reasons will now be described.

FIG. 18 shows a pre-peak curve of acidity measurement by voltammetry of a conventional electrolyte solution containing a naphthoquinone derivative. FIG. 19 shows a peak curve of acidity measurement by voltammetry of the conventional electrolyte solution containing a naphthoquinone derivative. FIG. 20 shows an oxygen reduction curve obtained in acidity measurement by voltammetry of an electrolyte solution. When the voltammetry is performed after removal of the dissolved oxygen in the electrolyte solution, the potential-current curve (hereinafter, referred to as the "voltammogram") which represents the result of synthesizing the pre-peak curve and the peak curve can be obtained, and thus the pre-peak appears clearly. In contrast, when the dissolved oxygen is not removed, the voltammogram represents the result of synthesizing the pre-peak curve, the peak curve and the oxygen reduction curve. This is a conceivable reason why the pre-peak does not appear clearly. The acidity measurement is difficult by the conventional method unless the electrolyte solution is deoxidized. In order to deoxidize the electrolyte solution, the acidity measuring apparatus is provided with a device for continuously supplying gas (e.g., nitrogen) to the acidity measuring apparatus. Such a structure enlarges the size of the acidity measuring apparatus, which prevents this method from being put into practical use.

In the field of measuring the lipid component in serum, a different substance from the substance to be measured is measured after several stages of reaction, since there is conventionally no appropriate method available for directly measuring the fatty acid or organic acid in the solution. The measurement of serum will be described in detail below.

The number of people obtaining a value outside the normal value range during the examination of the concentration of cholesterol, neutral fat (glycerin fatty acid ester), or phospholipid in serum is rapidly increasing due to increased consumption of American and European style food, increasing opportunities of drinking alcoholic drinks, lack of physical exercise, stress, or the like. Among the lipid components, the cholesterol level is used as a risk factor indicator of lifestyle-related diseases such as diabetes, arterial sclerosis, or hypothyroidism. The value of the neutral fat (glycerin fatty acid ester) is used as a risk factor indicator of lipid dysbolism, cerebrovascular accident, cardiac infarction, angina pectoris, and diabetes. The value of the lipid components is also used as a risk factor indicator of lipid dysbolism, cerebrovascular accident, cardiac infarction, angina pectoris, and diabetes, and also acts as a health risk factor indicator of hepatopathy obliterans, hyperthyroidism, and fulminant hepatitis.

Conventionally, the lipid components used as an indicator of the above-mentioned diseases are measured mainly by an enzyme method. In other words, a lipid component is decomposed into fatty acid and other components by an enzyme, and the components which are not fatty acids are measured. For example, the neutral fat is measured in the following manner. Serum is treated by lipoprotein lipase as an enzyme to decompose the neutral fat into glycerol and trifatty acid. Then, glycerolkinase as an enzyme for treating the glycerol, magnesium ions and adenosine triphosphatase (ATP) are added to decompose the glycerol into glycerol-1-phosphate and adenosine diphosphatase (ADP). Next, glycerol-1-phosphate oxidase as an enzyme for treating the glycerol-1-phosphate is added to decompose the glycerol-1-phosphate into dihydroxyacetone-1-phosphate and hydrogen peroxide. Finally, the peroxidase for treating the hydrogen peroxide and 4-aminoantipyrine and dimethyl aniline are added to generate a red quinone dye. The amount of the red quinone dye (corresponding to the amount of hydrogen peroxide) is measured, and the amount of neutral fat is obtained by calculation. The results of the above-described reactions are obtained with about 3 to 20 $\mu$L of serum.

The reason why the hydrogen peroxide obtained after the plurality of reaction stages is measured is that the neutralization titration and the technology disclosed in Japanese Laid-Open Publication No. 5-264503 are both difficult to apply to serum treated by an enzyme such as lipoprotein lipase, since the change of color caused by the indicator is difficult to read in the case of serum, and also since the serum contains oxygen.

As described above, by the conventional acidity measuring method, which uses the neutralization titration method, the observer monitoring the color change caused by the phenolphthalein indicator determines when the end point is reached. Accordingly, the end points vary and thus the acidity varies depending on the operator.

According to the neutralization titration defined by the Standard Methods for the Analysis of Oils, Fats and Derivatives used for measuring the fatty acid, a mixed solution containing ether and ethanol is used as the neutral solvent. Ether having a boiling point of as low as 34.6° C. is difficult to handle. Moreover, in the case where the sample has a dark color, such as oil which has been used for frying a large amount of food, or juice or wine which are originally dark colored, the color change caused by the phenolphthalein indicator near the end point cannot be accurately recognized. Thus, the measured value fluctuates. Furthermore, one cycle of measurement requires as much as 100 mL of neutral solvent and as much as 10 grams of sample. Also, the more measurement is performed, the greater the cost.

According to the above-described technology for measuring the lipid component in serum, treatment by enzyme is performed in 3 or 4 steps for any lipid component. Different components require different enzymes and a large amount of samples, which makes the operation excessively troublesome. Moreover, the results cannot be obtained until 3 to 4 stages of reactions are finished. In the case where an error occurs, it takes time to find in which stage the error occurred. Hydrogen peroxide as a target of measurement is unstable, and thus an error can possibly be generated unless the operation is performed quickly.

The technology disclosed in Japanese Laid-Open Publication No. 5-264503 has the following problem. In the case where a naphthoquinone derivative is used without removing oxygen from the electrolyte solution in order to reduce the size of the acidity measuring apparatus, a current is generated by the reduction of the oxygen dissolved in the solution, and the value of such a current overlaps the current value of acid to be measured as illustrated in FIG. 17. In the case where a small amount of acid is measured, the measured value fluctuates depending on the amount of dissolved oxygen, thus decreasing reliability. When a device for supplying gas is provided for removing the oxygen, the entire apparatus is enlarged and becomes difficult to handle. Thus, such an apparatus is difficult to put into practical use.

Moreover, by the above-described technology disclosed in Japanese Laid-Open Publication No. 5-264503, the electrolyte solution contains a protic organic solvent. The oil actually used and deteriorated by heat is hardly dissolved in the protic organic solvent (e.g., propanol, methanol, or ethanol). Even the use of a stirrer does not work. Accordingly, after the solution containing oil is stirred sufficiently, the oil layer is separated and removed by centrifugation, and the remaining solution is used as the electrolyte solution. The use of a centrifuge inevitably enlarges the entire apparatus. Furthermore, since the electrolyte solution is extracted from the solution containing oil, the measured value fluctuates when the solution containing oil is not stirred sufficiently. Accordingly, a reliable acidity measuring apparatus cannot be realized as in the case with the neutralization titration method. The technology involves difficult problems to solve before it can be embodied as an actual measuring apparatus although being superior in terms of principle.

As disclosed in Japanese Laid-Open Publication No. 5-264503, quinones other than naphthoquinone are conventionally considered to be too unstable to be used for accurate acidity measuring. The quinones are unstable to light even in the form of crystals, and are especially susceptible to photolysis when they are in the form of a solution. Specifically, the color of a solution containing benzoquinone changes into reddish purple when exposed to sunshine, and new absorption maximums are generated in the range of the ultraviolet and visible light. Since such a decomposition is facilitated in the case of an organic solvent, use of benzoquinone is conventionally considered to cause photolysis to prevent accurate measurement. Accordingly, the method of using a naphthoquinone derivative is conventionally considered to be the only possible method, and the problems of the dissolved oxygen involved in the use of the naphthoquinone derivative are difficult to solve.

SUMMARY OF THE INVENTION

According to one aspect of the invention, an acidity measuring apparatus includes a measuring container for accommodating an electrolyte solution including one of a 1,2-benzoquinone derivative and a 1,4-benzoquinone derivative, an organic solvent, an electrolyte and an acid-containing subject for measurement; a working electrode, a counter electrode and a reference electrode section provided in the measuring container and immersed in the electrolyte solution; and a control section for sweeping a potential of the working electrode within a prescribed range and for detecting a pre-peak value of a current generated by the acid and flowing in a circuit including the working electrode and the counter electrode. Accordingly, the voltammogram of the 1,2-benzoquinone derivative or the 1,4-benzoquinone derivative appears in an area far from and positive with respect to the area where reduction curve of the dissolved oxygen appears. Since this is swept by the control section, the influence of the reduction of the dissolved oxygen can be prevented when measuring the value of the pre-peak current.

In one embodiment of the invention, the subject for measurement is oil, and the acid is a free fatty acid in the oil. Accordingly, the degree of deterioration of oil can be estimated by measuring the free fatty acid in the oil.

In one embodiment of the invention, the subject for measurement is concentrated fruit juice, and the acid is an organic acid contained in the concentrated fruit juice. Accordingly, the temperature and water level can be appropriately set for cultivating fruits by measuring the organic acid contained in the concentrated fruit juice.

In one embodiment of the invention, the subject for measurement is juice, and the acid is an organic acid contained in the juice. Accordingly, the taste of the juice can be adjusted and quality control can be performed by measuring the organic acid contained in the fruit juice.

In one embodiment of the invention, the subject for measurement is an alcoholic drink, and the acid is an organic acid contained in the alcoholic drink. Accordingly, the taste of the alcoholic drink can be adjusted and quality control can be performed by measuring the organic acid contained in the alcoholic drink.

In one embodiment of the invention, the subject for measurement is a serum treated by an enzyme, and the acid is a fatty acid freed by dissolving a lipid component in the serum by an enzyme. Accordingly, the lipid component in the serum can be directly calculated by measuring the fatty acid in the serum containing fatty acid freed by dissolving a lipid component by the enzyme.

In one embodiment of the invention, the reference electrode section includes a reference electrode which is formed of silver—silver chloride. Accordingly, the electrode can be produced relatively easily at lower cost.

In one embodiment of the invention, the prescribed range is between +500 mV to −300 mV with respect to a potential of the reference electrode. Accordingly, the value of the pre-peak current of the voltammogram indicating the acidity can be stably measured without influence from the dissolved oxygen.

In one embodiment of the invention, the potential is swept within the prescribed range at a rate of 3 to 20 mV/second. Accordingly, a stable reading for the voltammogram can be obtained.

In one embodiment of the invention, the 1,2-benzoquinone derivative has side chains at positions 3 and 5 of the benzene ring. Accordingly, stable measurement can be performed with quinones other than a naphthoquinone derivative with no photolysis.

In one embodiment of the invention, the 1,2-benzoquinone derivative is 3,5-di-tert-butyl-1,2-benzoquinone. Accordingly, stable measurement can be performed with quinones other than a naphthoquinone derivative with no photolysis.

In one embodiment of the invention, the 1,4-benzoquinone derivative has side chains at positions 2 and 6 of the benzene ring. Accordingly, stable measurement can be performed with quinones other than a naphthoquinone derivative with no photolysis.

In one embodiment of the invention, the 1,4-benzoquinone derivative is 2,6-dimethyl-1,4-benzoquinone. Accordingly, stable measurement can be performed with quinones other than a naphthoquinone derivative with no photolysis.

In one embodiment of the invention, the electrolysis is lithium perchloride soluble in an organic solvent. Accordingly, the mobility of electrons in the electrolyte solution can be easily enhanced.

In one embodiment of the invention, the counter electrode is formed of a corrosion-resistant conductive material. Accordingly, the counter electrode is significantly resistant against corrosion and electrolysis can be stably performed with no substantial maintenance.

In one embodiment of the invention, the corrosion-resistant conductive material is one of platinum, graphite, gold, stainless steel, aluminum, and an alloy thereof. Accordingly, stable resistance against corrosion and low resistance are shown and energy can be saved.

In one embodiment of the invention, an inner liquid in the reference electrode section is a solution containing one of silver chloride, potassium chloride, sodium chloride, lithium chloride, copper sulfate, and silver nitrate. Accordingly, oxidation-reduction reaction of the reference electrode can be stably obtained with an aqueous solvent.

In one embodiment of the invention, an inner liquid in the reference electrode section is a solution containing acetonitrile. Accordingly, oxidation-reduction reaction of the reference electrode can be stably obtained even with an organic solvent.

In one embodiment of the invention, the acidity measuring apparatus further includes a liquid communication section for electrically connecting the electrode of the reference electrode section and the electrolyte solution, and the liquid communication section is formed of a porous ceramic material. Accordingly, the liquid communication section does not permit the electrolyte solution to pass therethrough but allows electrons and ions to pass therethrough.

In one embodiment of the invention, the acidity measuring apparatus further includes a salt bridge section for electrically connecting the electrode of the comparative electrode section and the electrolyte solution, and the salt bridge section is formed of a porous glass material. Accordingly, the salt bridge section does not permit the electrolyte solution to pass therethrough but allows electrons and ions to pass therethrough.

In one embodiment of the invention, the working electrode is formed of one of carbon and glassy carbon. Accordingly, sufficient electrons can be donated and accepted on the surface of the electrode without causing oxidation-reduction reaction of the solvent itself.

In one embodiment of the invention, the organic solvent is an ethanol-isooctane mixture solvent containing isooctane in the range of 35% to 70%. Accordingly, even oil which has been used and deteriorated by heat can be dissolved in the electrolyte solution.

In one embodiment of the invention, the organic solvent is ethanol. Accordingly, acidity of instant coffee dissolved in coffee, juice other than concentrated juice reduced in water, and alcoholic drink can be measured without precipitation or separation of the solution.

In one embodiment of the invention, the organic solvent is a mixture solvent containing ethanol, water and isopropylalcohol. Accordingly, all aqueous substances can be measured, without precipitation or separation of the solution. An aqueous electrolyte can be used without causing, for example, sodium chloride to be deposited. Even when the solvent is to be stored in a great amount, ethanol can be used safely because it is diluted with water.

In one embodiment of the invention, the acidity measuring apparatus further includes an acidity calculation device for calculating an acidity from the pre-peak current value. Accordingly, the acidity can be found immediately.

According to another aspect of the invention, a method for measuring an acidity of an acid-containing subject includes the steps of performing voltammetry of the electrolyte solution including the acid-containing subject for measurement; and measuring the value of a pre-peak current flowing in the electrolyte solution. The pre-peak appears at a potential which is positive with respect to a potential at which a peak of reduction of oxygen dissolved in the electrolyte solution appears. Accordingly, the value of the pre-peak current flowing in the electrolyte solution can be measured with no influence from the dissolved oxygen.

In one embodiment of the invention, the electrolyte solution includes one of a 1,2-benzoquinone derivative and a 1,4-benzoquinone derivative. Accordingly, the position at which the reduction current of the dissolved oxygen appears can be far from the position at which the pre-peak appears.

Thus, the invention described herein makes possible the advantages of (1) providing a compact and easy-to-use acidity measuring apparatus for realizing accurate and precise measurement of acidity with no need of oxygen removal, and (2) providing a method for measuring an acidity with sufficiently high accuracy and precision with no need of oxygen removal.

These and other advantages of the present invention will become apparent to those skilled in the art upon reading and understanding the following detailed description with reference to the accompanying figures.

DESCRIPTION OF THE PREFERRED EMBODIMENTS

Embodiment 1

An acidity measuring apparatus 100 in one embodiment according to the present invention will be described with reference to FIGS. 1 through 16.

Figure 1:
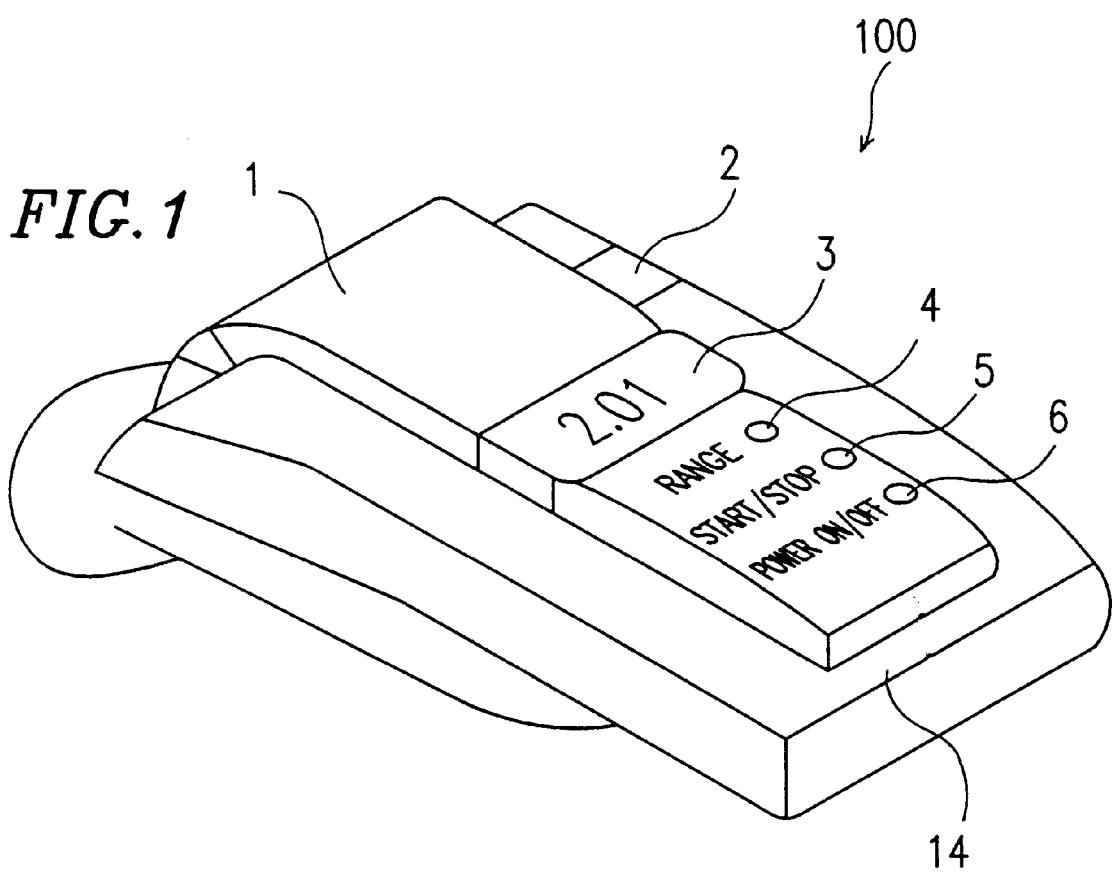
FIG. 1 is an external isometric view of an acidity measuring apparatus in one embodiment according to the present invention.

FIG. 1 is an external isometric view of the acidity measuring apparatus 100. As shown in FIG. 1, the acidity measuring apparatus 100 includes a top lid 1 for covering a measuring section 26, a button 2 for opening the top lid 1, an LCD (liquid crystal display) 3 for displaying acidity as a result of measurement, a button 4 for switching a range in accordance with the acidity, a start/stop button 5 for starting and stopping measurement, a power on/off button 6 for turning the power on and off, and a main body cover 14. The top lid 1 includes a connector (contact) for electrically connecting the measuring section and various electrodes, and the connecter is connected to a substrate.

Figure 2:
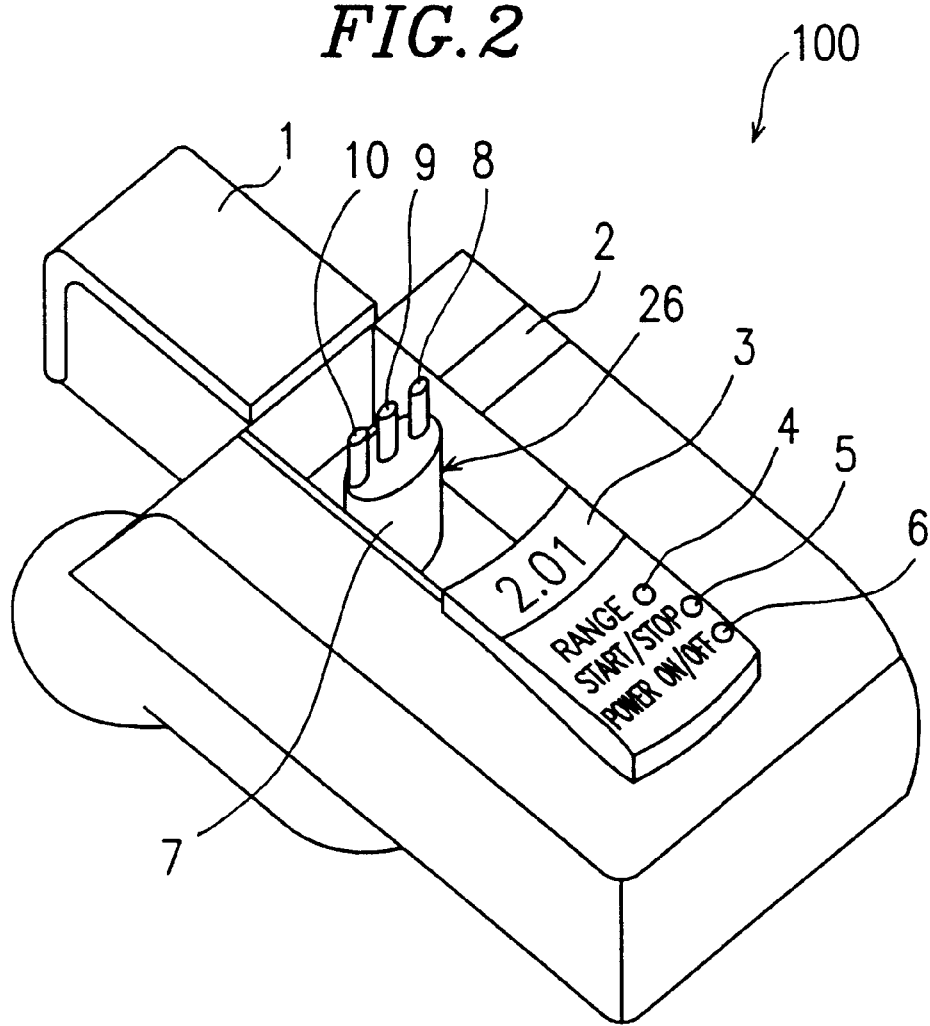
FIG. 2 is an isometric view of the acidity measuring apparatus shown in FIG. 1 in the state where a top lid is opened.

FIG. 2 is an isometric view of the acidity measuring apparatus 100 in the state where the top lid 1 is slid to be opened. In an inner space of the acidity measuring apparatus 100 below the top lid 1, the measuring section 26 is accommodated.

Figure 3:
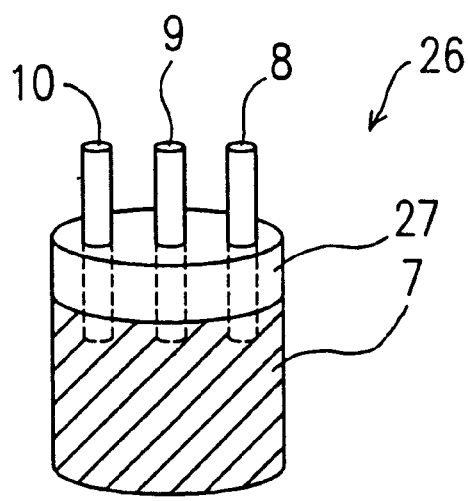
FIG. 3 is an isometric view of a measuring section of the acidity measuring apparatus shown in FIG. 1.

FIG. 3 is an isometric view of the measuring section 26. As shown in FIGS. 2 and 3, the measuring section 26 includes a measuring container 7 for accommodating an electrolyte solution containing a 1,2-benzoquinone derivative or a 1,4-benzoquinone derivative, an organic solvent, an electrolyte, and a subject for measurement in a mixed state. The measuring section 26 further includes a counter electrode 8, a working electrode 9, and a reference electrode section 10. As shown in FIG. 3, a container cover 27 provided with the counter electrode 8, the working electrode 9 and the reference electrode section 10 is attached to the measuring container 7. The counter electrode 8, the working electrode 9 and the reference electrode section 10 are immersed in the electrolyte solution.

The counter electrode 8 is preferably formed of platinum, graphite, or gold, all of which are chemically stable and are not corrodible even in the electrolyte solution. The counter electrode 8 can also be formed of, for example, stainless steel, aluminum or an alloy thereof, which are not corroded. The working electrode 9 is preferably formed of carbon, glassy carbon, or PFC (plastic formed carbon) obtained by sintering plastic foam at a temperature in the range of about 1,000° C. to about 2,000° C.

Figure 4:
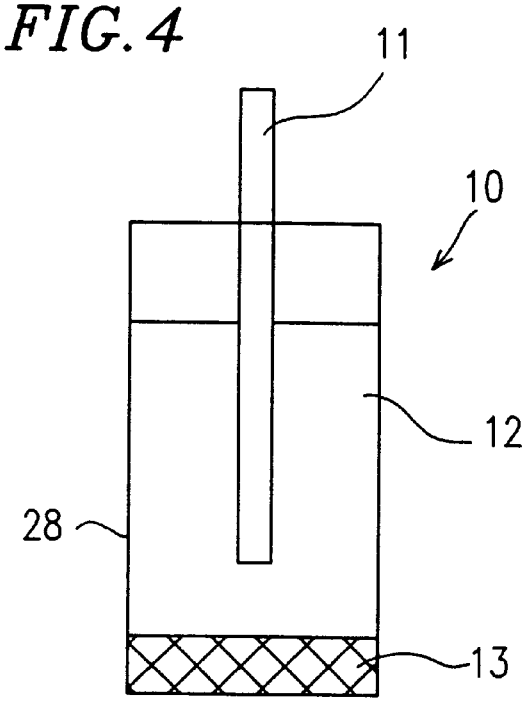
FIG. 4 is a detailed view of a reference electrode section of the acidity measuring apparatus shown in FIG. 1.

FIG. 4 is a detailed view of the reference electrode section 10. As shown in FIG. 4, the reference electrode section 10 includes the glass container 28, a reference electrode 11 projecting into a glass container 28, an inner liquid 12 accommodated in the glass container 28, and a salt bridge section 13 provided plugging the end of the glass container 28. The reference electrode 11 is preferably formed of silver—silver chloride, but can also be formed of saturated calomel, silver—silver ion, or mercury-saturated mercury sulfate. The phrase, for example, "silver—silver chloride" refers to coating a surface of the reference electrode 11 formed of silver with silver chloride. The inner liquid 12 is preferably a chloride such as silver chloride, potassium chloride, sodium chloride, or lithium chloride; acetonitrile; copper sulfate; silver nitrate; or any other solvent or solution which exhibits a buffer function in an oxidation-reduction reaction. The salt bridge section 13, which is positioned between the inner liquid 12 and the electrolyte solution, does not permit the inner liquid 12 or the electrolyte solution to pass therethrough but allows electrons and ions to pass therethrough. The salt bridge section 13 is formed of, for example, a porous ceramic material or porous glass (e.g., Vycol manufactured by Corning, Inc.,). Although not shown in FIG. 1 or 2, the acidity measuring apparatus 100 includes a connector for connecting the counter electrode 8, the working electrode 9, and the reference electrode section 10 to a control circuit (not shown in FIGS. 1 through 4) described below.

The electrolyte solution accommodated in the measuring container 7 contains lithium perchloride as the electrolyte for measuring an acid value of edible oil in the present embodiment. The usable electrolyte can vary in accordance with the type of the subject for measurement, and include, for example, potassium chloride (KCl), sodium chloride (NaCl), or lithium chloride (LiCl). The electrolyte solution in the present embodiment is prepared by dissolving 10 mM (millimole/liter) 1,2-benzoquinone derivative and 50 mM lithium perchloride in 10 mL of mixed solvent containing 65% of ethanol and 35% of isooctane, and then mixing the subject for measurement with the resultant liquid. Ethanol can relatively easily dissolve the electrolyte and also washes the surface of the electrode. Isooctane can dissolve even heat-deteriorated oil and is soluble in ethanol. Since the heat-deteriorated oil is not dissolved in the mixture solvent unless isooctane is present in the amount of 35% or more, the isooctane is contained in the mixture solvent is preferably in the range of 35% to 70%, and more preferably in the range of 45% to 55%. When the degree of deterioration of the oil is excessively raised, it is preferable to slightly increase the content of isooctane accordingly. Due to isooctane being present in the amount of 35% or more, the mixed solvent in the present embodiment can dissolve the heat-deteriorated oil even though the mixed solvent contains ethanol, which is a protic organic solvent, and the acidity of the oil can be measured without performing stirring and centrifugation as is required by a conventional apparatus.

The acidity of all aqueous substances including instant coffee dissolved in water and concentrated juice reduced by water can be measured, without precipitation or separation of the solution, by using a solvent containing 10% to 40% of isopropylalcohol, 10% to 40% of water, and 50% to 70% of ethanol, preferably 15% to 25% of isopropylalcohol, 15% to 25% of water, and 55% to 65% of ethanol (referred to as "solvent 1"). Considering that the range of alcohol present in the disinfecting ethanol commonly used defined by the Japanese Pharmacopoeia is 76.9% to 81.4%, solvent 1 can be safely stored. With solvent 1, sodium chloride can also be used as the electrolyte after dilution with water.

In the case of measuring the acidity of instant coffee dissolved in water, juice other than concentrated juice reduced in water, and alcoholic drinks, a 100% ethanol solvent (referred to as "solvent 2") can also be used. Since the solubility of quinone with respect to solvent 2 is sufficiently large and results in a higher electrochemical property than that obtained when solvent 1 is used, even if the same amount of quinone is used. No precipitation or solution separation occurs. The reason is that more reactions occur in the case of solvent 2 due to a higher diffusion rate of quinone in solvent 2 than in solvent 1.

In the case of solvent 1, when the mixture ratio of isopropylalcohol, water and ethanol is varied, the required amount of quinone also varies. Accordingly, regardless of which solvent (1 or 2) is used, it is necessary to select the solvent in consideration of the properties of the subject to be measured.

Figure 5:
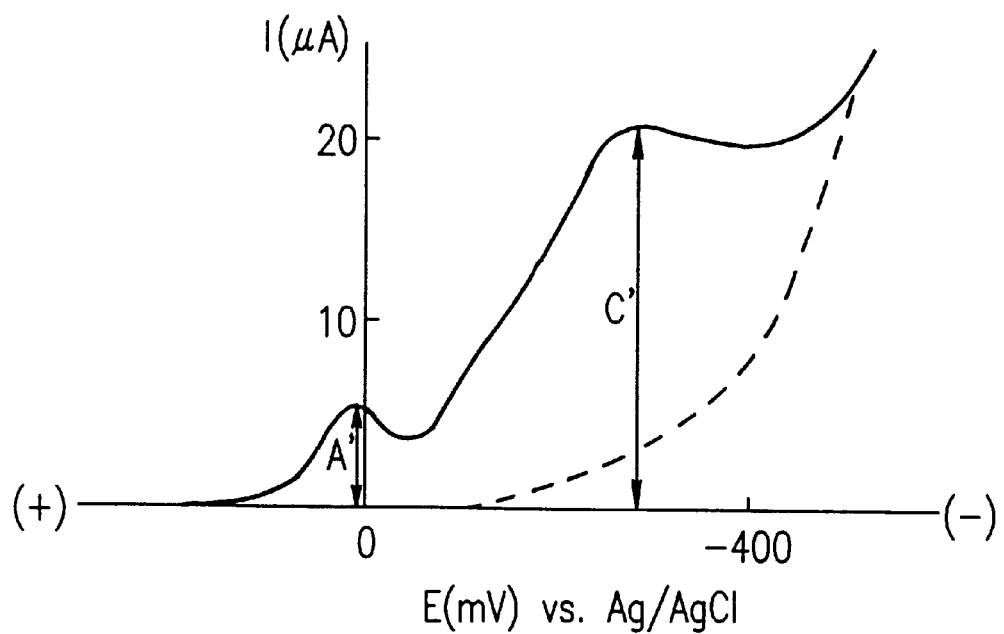
FIG. 5 is a graph illustrating the current vs. potential relationship for acidity measurement by voltammetry of an electrolyte solution containing a 1,2-benzoquinone derivative.

According to the present invention, the electrolyte solution contains a 1,2-benzoquinone derivative or a 1,4-benzoquinone derivative. FIG. 5 is a graph illustrating the current vs. potential relationship for acidity measurement by voltammetry of the electrolyte solution containing a 1,2-benzoquinone derivative. In FIG. 5, the axis of abscissas represents the potential of the working electrode 9 with respect to the potential of the reference electrode section 10 when the reference electrode 11 is formed of silver—silver chloride and the working electrode 9 is formed of $\phi 2$ plastic formed carbon. The axis of ordinates represents the current flowing in the circuit including the working electrode and the counter electrode 8 at this time. It should be noted that the value of the current varies in accordance with conditions such as the surface area of the working electrode 9 and acid concentration. The position where the potential peak appears along the axis of abscissas slightly fluctuates in accordance with the acid concentration, which is negligible.

As shown in FIG. 5, the voltammogram of the 1,2-benzoquinone derivative having side chains on the benzene ring appears in the area which is far positive respect to the area where reduction curve of the dissolved oxygen appears. The solid line represents the voltammogram of 1,2-benzoquinone derivative, and the dotted line represents the reduction current of the dissolved oxygen. As can be appreciated from FIG. 5, the pre-peak curve appears in the area positive with respect to the vicinity of 0 mV (indicated by letter A') and is shifted by about 400 mV from the reduction curve of the dissolved oxygen. Even at the position of a main peak of the quinone (indicated by letter C'), there is little influence of the reduction of the dissolved oxygen. Since the pre-peak value can be measured in the area where there is no influence of the dissolved oxygen, the acidity can be measured accurately and precisely with no influence of dissolved oxygen and thus with no fluctuation even when the dissolved oxygen is not removed prior to the measurement.

Figure 6:
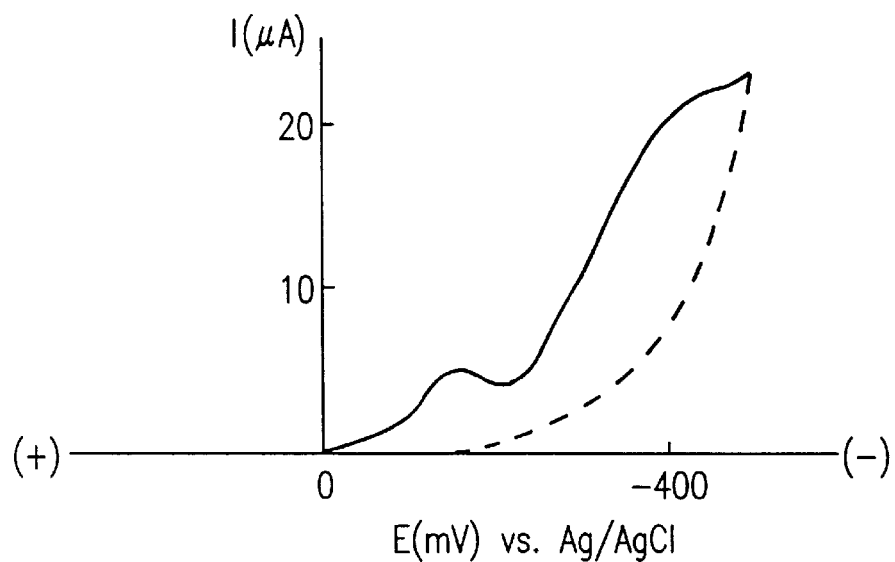
FIG. 6 is a graph illustrating the current vs. potential relationship for acidity measurement by voltammetry of an electrolyte solution containing a 1,4-benzoquinone derivative.

FIG. 6 is a graph illustrating the current vs. potential relationship for acidity measurement by voltammetry of the electrolyte solution containing a 1,4-benzoquinone derivative. As shown in FIG. 6, the pre-peak of the voltammogram of the 1,4-benzoquinone derivative having side chains on the benzene ring appears at a position which partially overlaps the area where the reduction curve of the dissolved oxygen appears. The solid line represents the voltammogram of 1,4-benzoquinone derivative, and the dotted line represents the reduction curve of the dissolved oxygen. As can be appreciated from FIG. 6, the pre-peak is shifted by about 200 mV from the reduction curve of the dissolved oxygen. At the position of the main peak, a slight influence of the reduction of the dissolved oxygen is recognized, but such an influence is negligible for the measurement of acidity. Since the pre-peak current value can be measured in the area where there is very little influence of the dissolved oxygen, the influence of the dissolved oxygen is negligible even when the dissolved oxygen is not removed prior to the measurement, and thus the acidity can be measured accurately and precisely with no fluctuation.

Figure 7:
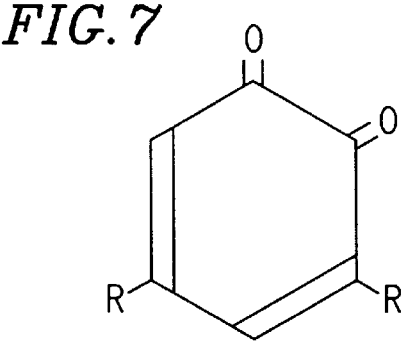
FIG. 7 shows a molecular structure of a 1,2-benzoquinone derivative having side chains R.
Figure 8:
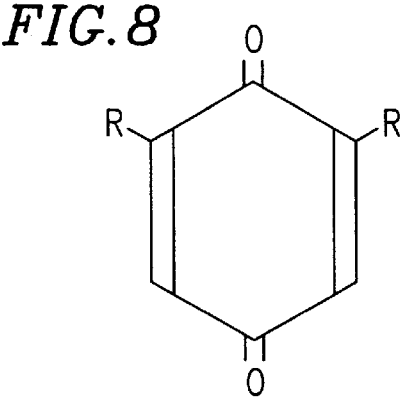
FIG. 8 shows a molecular structure of a 1,4-benzoquinone derivative having side chains R.
Figure 9:
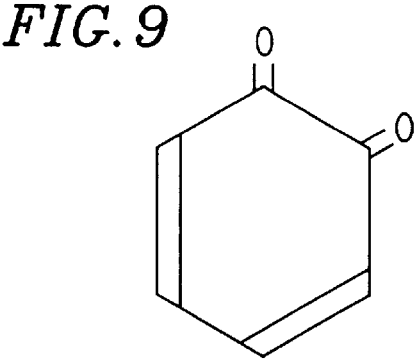
FIG. 9 shows a molecular structure of a 1,2-benzoquinone with no side chain.
Figure 10:
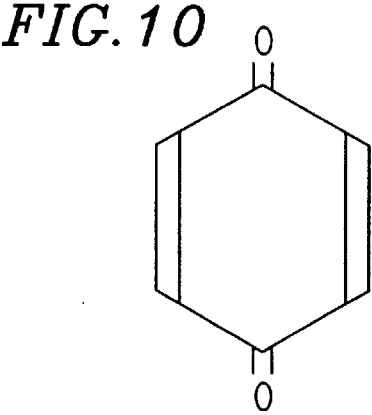
FIG. 10 shows a molecular structure of a 1,4-benzoquinone with no side chain.
Figure 11:
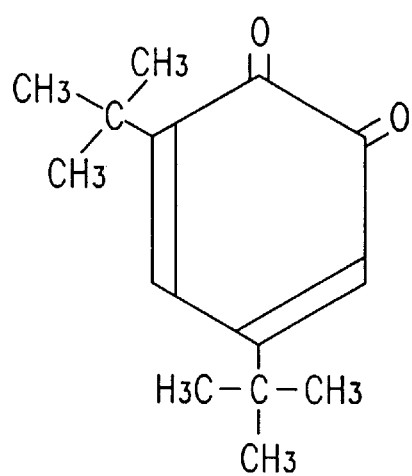
FIG. 11 shows a molecular structure of 3,5-di-tert-butyl-1,2-benzoquinone.
Figure 12:
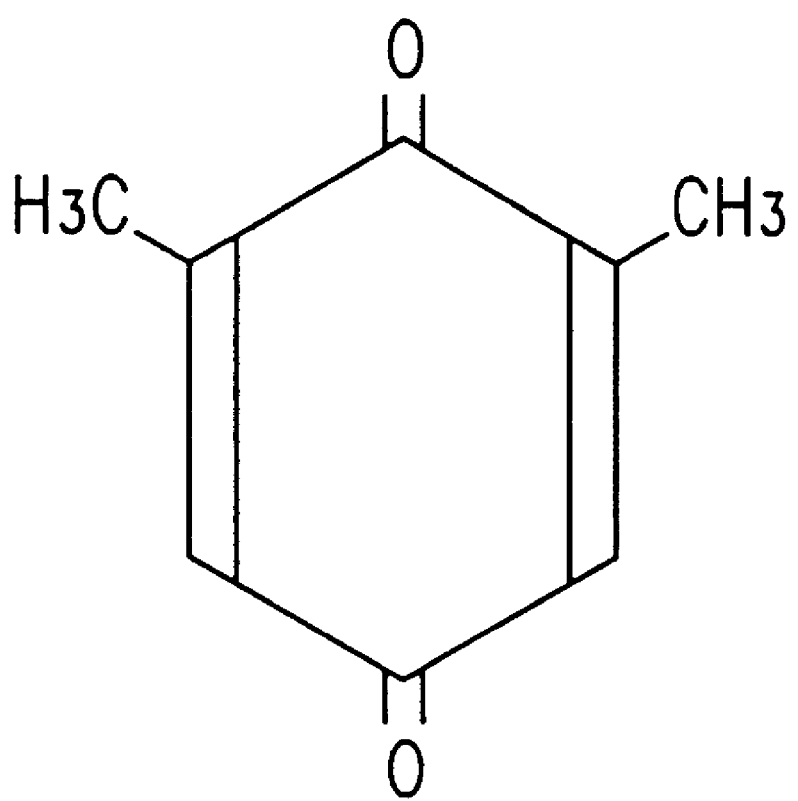
FIG. 12 shows a molecular structure of 2,6-dimethyl-1,4-benzoquinone.

The 1,2-benzoquinone derivative in the benzene ring and the 1,4-benzoquinone derivative both having side chains on the benzene ring have a property of allowing for stable measurement without causing photolysis, which is often caused in quinones, in addition to the property of having a pre-peak far from the reduction potential of the dissolved oxygen. FIG. 7 shows a molecular structure of a 1,2-benzoquinone derivative having side chains R, and FIG. 8 shows a molecular structure of a 1,4-benzoquinone derivative having side chains R. FIG. 9 shows a molecular structure of a 1,2-benzoquinone with no side chain, and FIG. 10 shows a molecular structure of a 1,4-benzoquinone with no side chain. The 1,2-benzoquinone derivative shown in FIG. 7 and the 1,4-benzoquinone derivative shown in FIG. 8, each of which has side chains R, are less susceptible to photolysis even if being supplied with a photolysis energy because such light energy is consumed as kinetic energy required for molecular stretching and contraction of the side chains R and molecular rotation of the side chains R. Preferable side chains R of the 1,2-benzoquinone derivative and the 1,4-benzoquinone derivative include a steric hindrance group (e.g., tert-butyl-cyclohexyl group). A more preferable 1,2-benzoquinone derivative is, for example, 3,5-di-tert-butyl-1,2-benzoquinone shown in FIG. 11. A more preferable 1,4-benzoquinone derivative is, for example, 2,6-dimethyl-1,4-benzoquinone shown in FIG. 12. When 3,5-di-tert-butyl-1,2-benzoquinone or 2,6-dimethyl-1,4-benzoquinone is used, a tert-butyl or methyl group donates electrons to the benzene ring due to their structure. Thus, the molecule of such a compound can easily have a conjugated structure. Also, the light energy is mostly absorbed, thus mostly preventing photolysis. For these reasons, stable measurement is realized. The above-described advantages cannot be obtained when 1,2-benzoquinone shown in FIG. 9 or 1,4-benzoquinone shown in FIG. 10 is used.

The stability of the quinones with respect to light and the separation of the pre-peak from the reduction curve of the dissolved oxygen in the voltammogram has the following relationship. When a quinone derivative such as naphthoquinone derivative having a relatively high stability with respect to light is used, the pre-peak gradually shifts in the direction of the negative potential side and finally overlaps the reduction curve of the dissolved oxygen. When a quinone derivative having a relatively low stability with respect to light is used, the pre-peak gradually shifts in such a direction so as not to overlap the reduction curve of the dissolved oxygen. However, the electrolyte solution itself is changed in quality by the influence of light, and thus the measured value fluctuates. Accordingly, the practicality of the electrolyte solution is deteriorated. A quinone derivative, having sufficient stability with respect to light and having a voltammogram which has a pre-peak not overlapping at least the reduction curve of the dissolved oxygen, is not influenced by the dissolved oxygen and thus has appropriate properties for the use as the electrolyte. Preferable such quinone derivatives are a 1,2-benzoquinone derivative having side chains at positions 3 and 5 of the benzene ring, specifically 3,5-di-tert-butyl-1,2-benzoquinone and a 1,4-benzoquinone derivative having side chains at positions 2 and 6 of the benzene ring, specifically, 2,6-dimethyl-1,4-benzoquinone. These derivatives realize stable measurement with no photolysis, and the voltammograms thereof have a pre-peak far from the reduction curve of the dissolved oxygen as shown in FIGS. 5 and 6.

Acidity is measured by the acidity measuring apparatus 100 in the present embodiment, for example, in the following manner with respect to FIGS. 1 through 4.

One half gram of heat-deteriorated oil as a subject for measurement is mixed with 10 mL of the electrolyte solution and then stirred. In the present embodiment, the electrolyte solution contains a 1,2-benzoquinone derivative or a 1,4-benzoquinone derivative, lithium perchloride as an electrolyte, and the mixed solvent of ethanol and isooctane. Next, the mixture is placed in the measuring container 7. Thereafter, the container cover 27, to which the counter electrode 8, the working electrode 9 and the reference electrode section 10 are attached, is fitted to the measuring container 7. The counter electrode 8, the working electrode 9 and the reference electrode section 10 are connected to a control circuit (not shown in FIGS. 1 through 4) used for voltammetry. The top lid 1 is closed to put the acidity measuring apparatus 100 in a measuring configuration. When the power on/off button 6 is pushed to turn the apparatus 100 on and the start/stop button 5 is pushed to start the measurement, a control section described below (not shown in FIGS. 1 through 4) of the control circuit applies a voltage between the working electrode 9 and the counter electrode 8 so that the potential of the working electrode 9 is swept with respect to the potential of the reference electrode 11 formed of silver—silver chloride in the range of +500 mV to −300 mV (preferably in the range of +200 mV to −200 mV) at a rate of 3 to 20 mV/second (preferably at a rate of 3 to 5 mV/second). In the range of +500 mV to −300 mV, there is very little influence from the dissolved oxygen and thus the pre-peak current value can be measured accurately and precisely. The range of sweeping is preferably +500 mV to −300 mV with respect to the potential of the comparative electrode 11 formed of silver—silver chloride. The potential of the reference electrode 11 formed of silver—silver chloride is +222 mV with respect to the standard hydrogen electrode potential proposed by Nernst. Accordingly, the preferable sweeping range in the latter case is +722 mV to −78 mV. In the case where the reference electrode 11 is formed of saturated calomel, the preferable sweeping range is +454 mV to −146 mV because the potential of the calomel electrode is +268 mV.

When a prescribed potential difference is swept at a rate of 3 to 20 mV/second, a stable voltammogram is obtained as described below and a peak of the reduction curve of the acid appears at a potential around 0 mV. This is a pre-peak, which shifts in the direction of the negative potential side as the acid concentration increases. Even though the pre-peak thus shifts, generally any acidity can be measured with no influence from the dissolved oxygen as long as the sweeping range is set to +500 mV to −300 mV with respect to the potential of the reference electrode 11 formed of silver—silver chloride.

Hereinafter, the control circuit 29 for controlling the operation of the acidity measuring apparatus 100 will be described with reference to FIG. 13.

Figure 13:
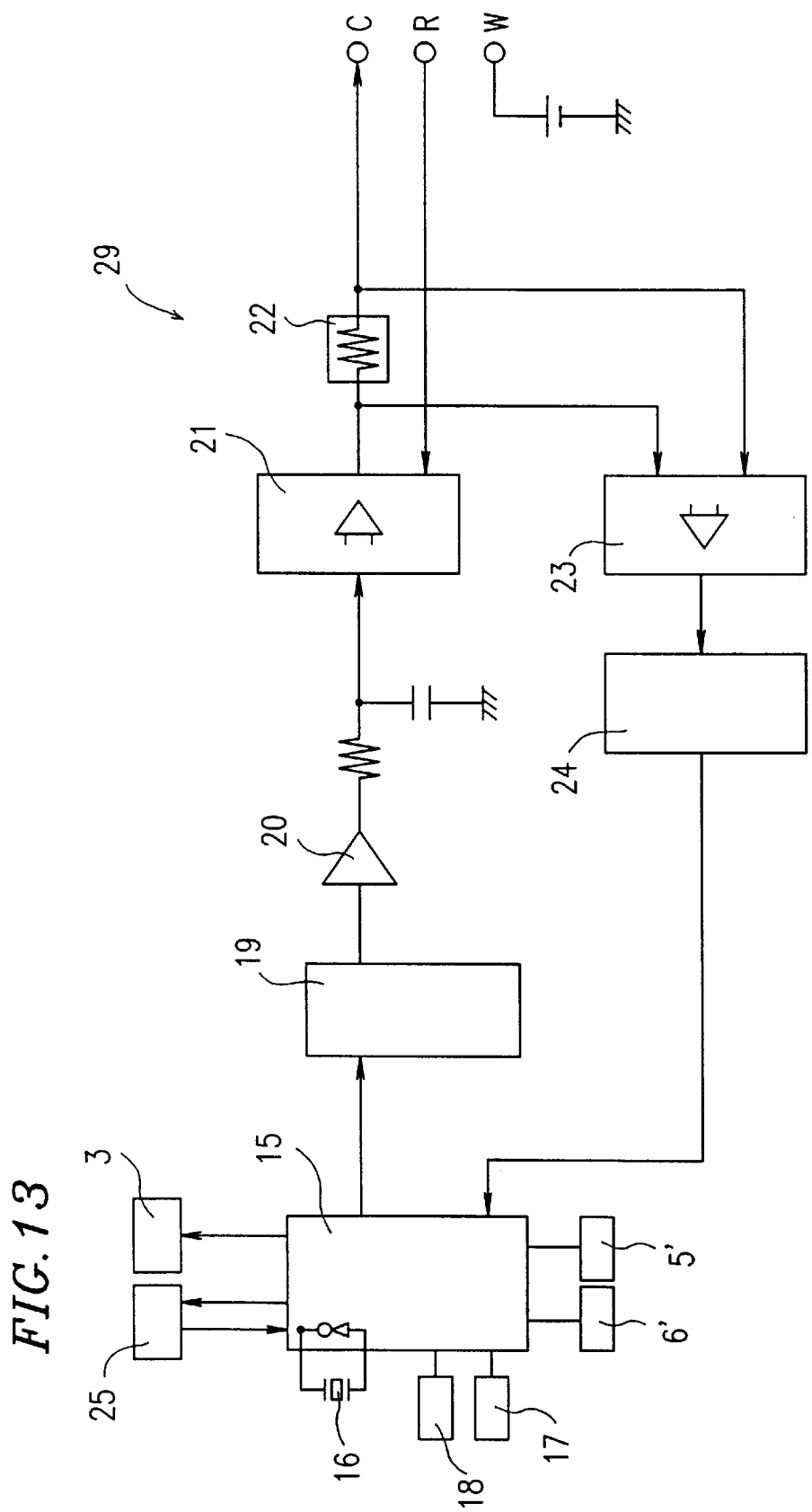
FIG. 13 is a block diagram of a control circuit of the acidity measuring apparatus shown in FIG. 1.

FIG. 13 is a block diagram of the control circuit 29. As shown in FIG. 13, the control circuit 29 includes a start/stop switch 5' operated by the start/stop button 5, a power on/off switch 6' operated by the power on/off button 6, a control section 15 including a microcomputer or the like, an oscillator 16, a frequency dividing circuit 17, a timer 18, a D/A converter 19, an operational amplifier 20, a monitoring circuit 21, a resistor 22, a differential amplifier 23, an A/C converter 24, and an acidity calculation device 25 including a microcomputer or the like.

When the power on/off button 6 (FIG. 1) is pushed, the LCD 3 is turned on to be in an operating state. When the start/stop button 5 is pushed, the control section 15 (FIG. 13) generates clocks therein by the frequency dividing circuit 17 based on a signal generated by the oscillator 16. The timer 18 starts counting the clocks. The timer 18 performs counting second by second. The control section 15 sends a digital signal (pulses) having a prescribed voltage to the D/A converter 19 in synchronization with the clocks counted by the timer 18. The D/A converter 19 converts the digital signal into an analog signal and outputs the analog signal to the operational amplifier 20.

Figure 14:
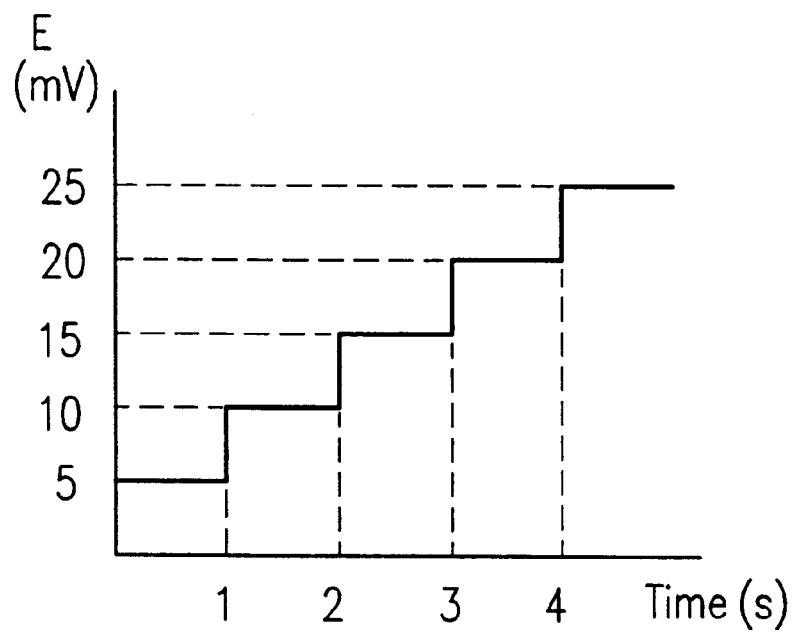
FIG. 14 is a graph illustrating an output from an operational amplifier of the control circuit shown in FIG. 13.

FIG. 14 shows the output from the operational amplifier 20 (FIG. 13). The axis of abscissas represents the time, and the axis of ordinates represents the voltage. As shown in FIG. 14, each time the time is counted as 1 second, 2 seconds, 3 seconds, . . . , the voltage varies as 5 mV, 10 mV, 15 mV, . . . . The signal output by the operational amplifier 20 (FIG. 13) is integrated and converted into an analog signal (FIG. 15) by an RC integration circuit. Then, the resultant signal is input to the monitoring circuit 21 (FIG. 13).

The monitoring circuit 21 controls a voltage C' (FIG. 5) of the counter electrode 8 in accordance with the analog signal using the imaginary shortcircuiting of an operation amplifier included in the monitoring circuit 21. The control is performed so that a voltage R at one input of the reference electrode 11 is equal to that of the analog signal. By such control, the potential difference between the reference electrode 11 and the working electrode 9 is in a prescribed range (e.g., +500 mV to −300 mV). The current flowing in the circuit including the working electrode and the counter electrode 8 and the potential difference between two ends of the resistor 22 are processed by the differential amplifier 23 to obtain an analog signal. The analog signal is converted into a digital signal by the A/D converter 24. Then, the digital signal is input to the control section 15.

Figure 15:
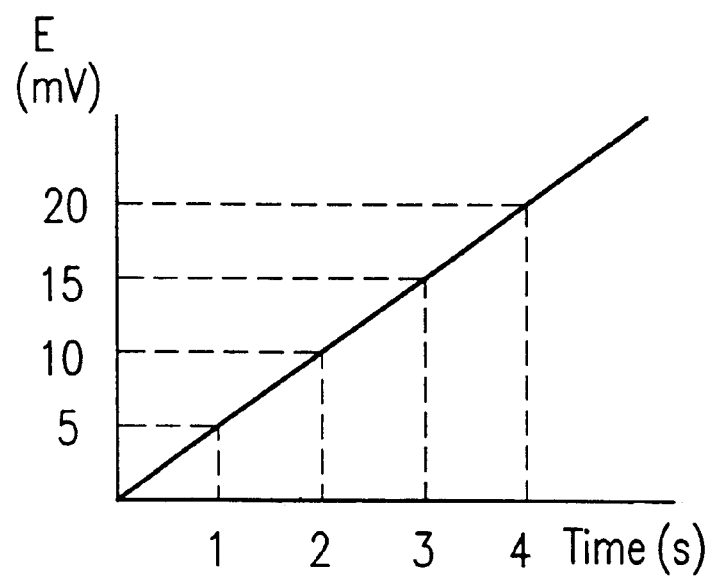
FIG. 15 is a graph illustrating an output from an integral circuit of the control circuit shown in FIG. 13.

The control section 15 compares each of the input current with a voltage swept at a prescribed rate as shown in FIG. 15, and thus detects a current value which provides the pre-peak indicated by letter A' in FIG. 5. In this embodiment, the electrolyte solution includes 3,5-di-tert-butyl-1,2-benzoquinone. Based on the value of the pre-peak current, the acidity calculation device 25 calculates the acidity, and the resultant value is displayed by the LCD 3.

Figure 16:
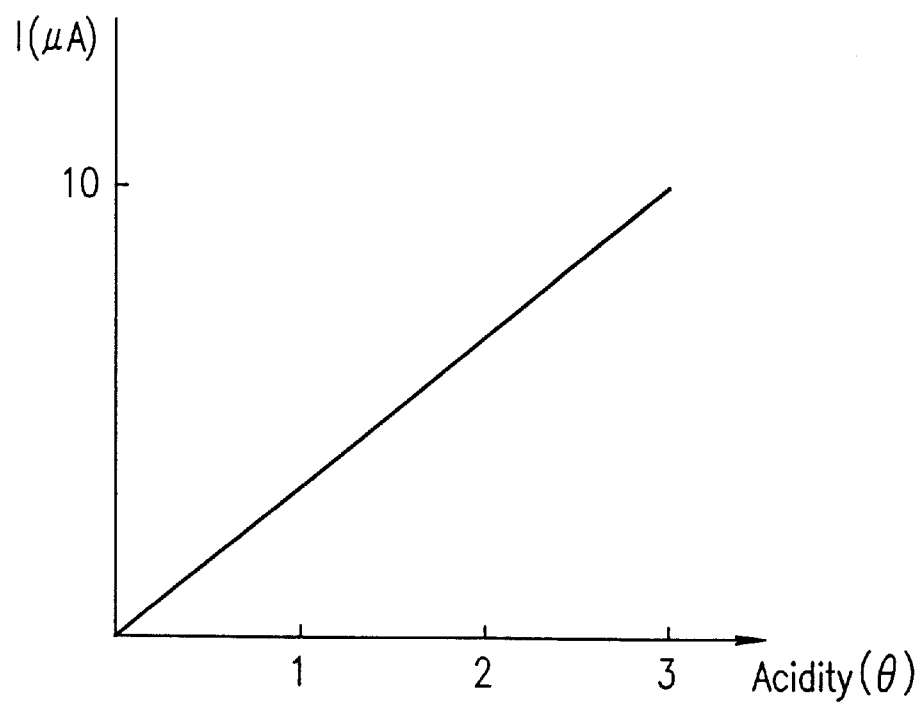
FIG. 16 is a graph illustrating the acidity vs. reduction current obtained by the acidity measuring apparatus shown in FIG. 1.
Figure 17:
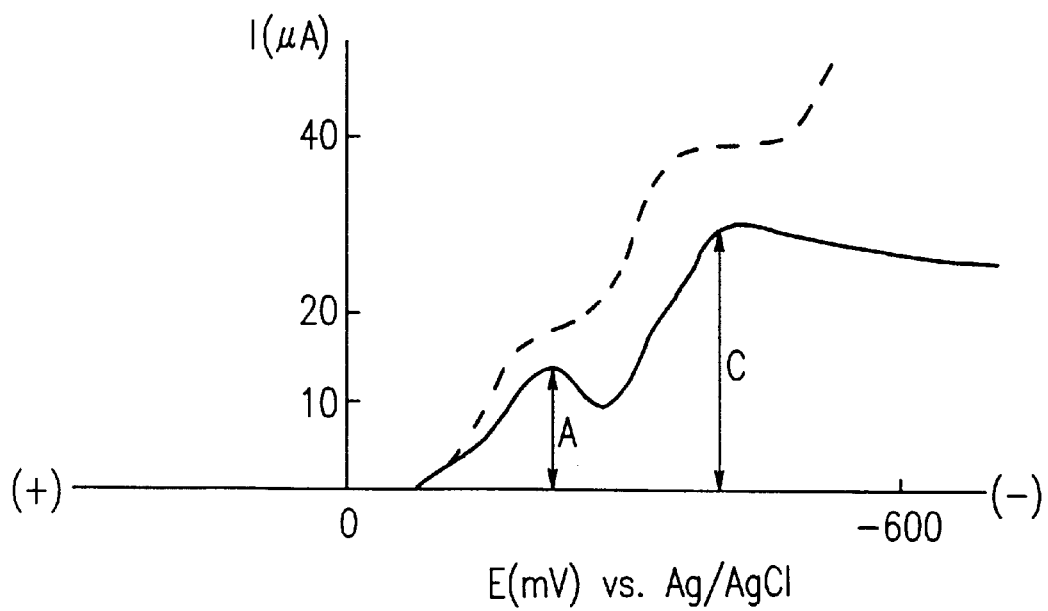
FIG. 17 is a graph illustrating the current vs. potential relationship for acidity measurement by voltammetry of an electrolyte solution containing a naphthoquinone derivative.
Figure 18:
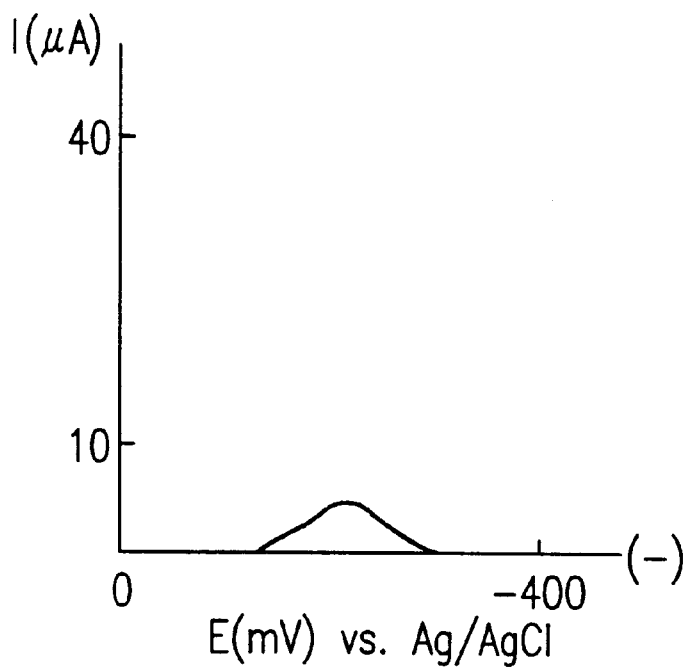
FIG. 18 is a graph illustrating a pre-peak current of acidity measurement by voltammetry of an electrolyte solution containing a naphthoquinone derivative.
Figure 19:
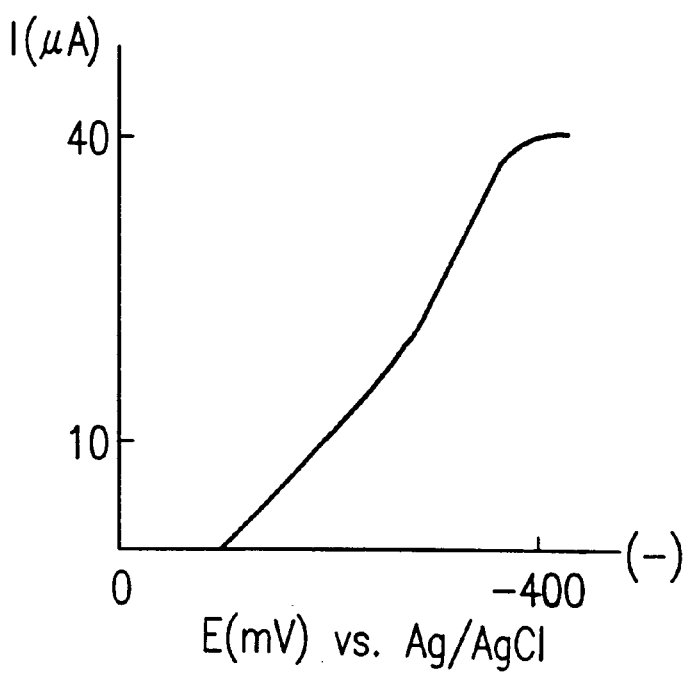
FIG. 19 is a graph illustrating a main peak of naphthoquinone by voltammetry of the electrolyte solution containing a naphthoquinone derivative.
Figure 20:
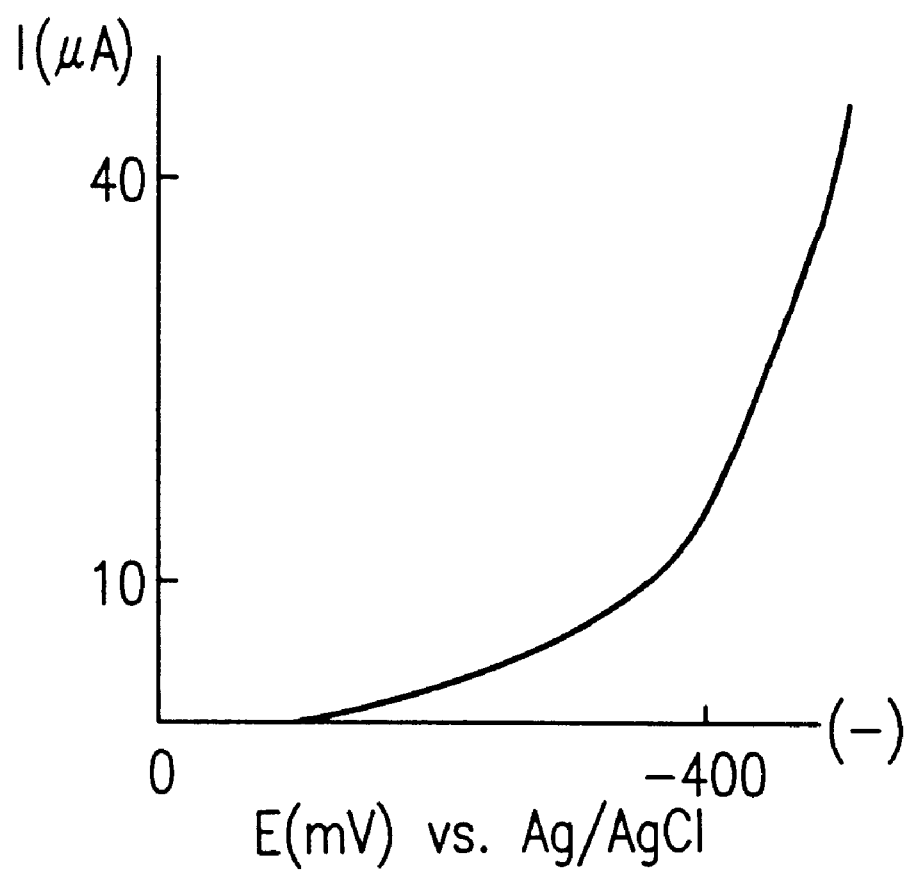
FIG. 20 is a graph illustrating an oxygen reduction curve obtained by voltammetry of an electrolyte solution.

In FIG. 5, the voltage value (indicated by letter E) is the difference between the potential of the working electrode 9 and the potential of the reference electrode 11 of the reference electrode section 10. The current value (indicated by letter I) flows in the circuit including the working electrode and the counter electrode 8. The current value I providing the pre-peak current value A' and the acidity e of the acid contained in the subject for measurement have a proportional relationship as shown in FIG. 16. In other words, when the current providing the pre-peak and the acidity have the relationship of $I=K\theta+C$ where K and C are constants. Accordingly, the acidity $\theta$ is measured by measuring the current value I.

The control section 15 applies a voltage between the working electrode 9 and the counter electrode 8 while monitoring the difference between the potential of the working electrode and the potential of the reference electrode 11 of the reference electrode section 10. In the case where the potential difference between the working electrode 9 and the reference electrode 11 is swept at a rate of more than about 20 mV/second, the electrode reaction is an electrochemically non-reversible reaction or an electrochemically quasi-reversible reaction due to the high sweeping rate. At this point, the potential at which the pre-peak appears shifts in the direction of the main peak, and thus the pre-peak and the main peak overlap. As a result, the pre-peak cannot be distinguished on the curve. In the case where the potential difference between the working electrode 9 and the reference electrode 11 is swept at a rate of less than about 3 mV/second, the reaction on the electrode is excessive. As a result, a stable current curve cannot be obtained. Accordingly, the sweeping rate is preferably in the range of 3 mV/second to 20 mV/second, and more preferably in the range of 3 mV/second to 5 mV/second. In the case where the solvent is a mixture of ethanol, water and isopropylalcohol, a stable current-potential curve can be obtained even when the potential is swept at the rate of 3 to 100 mV/second. In consideration of these results, a stable current-potential curve can be obtained whatever type of solvent is used as long as the potential is swept at the rate in the range of 3 mV/second to 20 mV/second.

In order to convert measured value to an acidity, the following method is preferred. A standard reagent, the acidity of which is already known, is produced. The relationship between the acidity (e.g., 1, 2, 3, . . . ) and the current level ($\mu A$), and the proportional constants K and C for each degree of acidity are stored in a memory of the acidity calculation device 25. By storing the constants K and C in this manner, when an arbitrary acidity is to be measured, the measured current value I can be converted into the acidity $\theta$ by the acidity calculation device 25 including a microcomputer.

Embodiment 2

In another embodiment according to the present invention, measurement of acidity of serum will be described. In the case where the subject for measurement is serum, pre-treatment (preferably, treatment by an enzyme) is required. In this embodiment, an enzyme reaction container is prepared with an enzyme contained therein. Serum is introduced into the reaction container. The lipid component in the serum is decomposed and free fatty acid is produced. In the case where the lipid component is, for example, neutral fat, lipoprotein lipase can be used as an enzyme. As a result, glycerol and free fatty acid are produced by hydrolysis. In the case where the lipid component is cholesterol (cholesterol fatty acid ester), cholesterol esterase can be used as an enzyme. As a result, free cholesterol and free fatty acid are produced by hydrolysis. In the case where the lipid component is phospholipid, phospholipase (phospholipase A) can be used as an enzyme. As a result, free fatty acid and phospholipid from which fatty acid has been removed are obtained.

After the free fatty acid is produced by the action of an enzyme in this manner, the serum is transferred from the enzyme reaction container to a measuring container for measurement. The free fatty acid is measured by the acidity measuring apparatus 100 (e.g., FIG. 1) in the first embodiment. Then, the amount of the original lipid component contained in the serum is calculated based on the measured acidity of the free fatty acid. The detailed structure of the acidity measuring apparatus 100 will not be described here. The above-described calculation function can be incorporated in the acidity calculation device 25 (FIG. 13).

As can be understood from the first and second embodiments, an acidity measuring apparatus according to the present invention uses an electrolyte solution containing a 1,2-benzoquinone derivative having side chains on the benzene ring or a 1,4-benzoquinone derivative having side chains on the benzene ring, an organic solvent, an electrolyte, and an acid-containing subject for measurement. Due to such an electrolyte solution, a compact apparatus for measuring the acidity accurately and precisely without removing the dissolved oxygen in the electrolyte solution can be realized. Moreover, due to the control section for sweeping the potential of the working electrode within a prescribed range with respect to the potential of the comparative electrode and also detecting the pre-peak value of the current, an acidity measuring apparatus according to the present invention can be relatively easy to operate, allows for automatic determination of the acidity, and provides accurate and precise acidity measurement.

Furthermore, the acidity of the oil which has been used and deteriorated by heat can also be sufficiently dissolved in the electrolyte solution, and thus a compact apparatus can be realized.

A method for measuring acidity of a subject realizes accurate and precise measurement with no need for removing the oxygen dissolved in the electrolyte solution.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An acidity measuring apparatus, comprising:
    a measuring container, wherein the measuring container contains an electrolyte solution including one of a 1,2-benzoquinone derivative and a 1,4-benzoquinone derivative both having side chains on the benzene ring, an organic solvent, an electrolyte and an acid-containing subject for measurement;
    a working electrode, a counter electrode and a reference electrode section provided in the measuring container and immersed in the electrolyte solution; and
    a control section for sweeping a potential of the working electrode within a prescribed range and for detecting a value of a pre-peak current generated by the acid and flowing between the working electrode and the counter electrode,
    wherein the 1,2-benzoquinone derivative is 3,5-di-tert-butyl-1,2-benzoquinone and the 1,4-benzoquinone derivative is 2,6-dimethyl-1,4-benzoquinone.

2. An acidity measuring apparatus according to claim 1, wherein the subject for measurement is oil, and the acid is a free fatty acid in the oil.

3. An acidity measuring apparatus according to claim 1, wherein the subject for measurement is concentrated fruit juice, and the acid is an organic acid contained in the concentrated fruit juice.

4. An acidity measuring apparatus according to claim 1, wherein the subject for measurement is juice, and the acid is an organic acid contained in the juice.

5. An acidity measuring apparatus according to claim 1, wherein the subject for measurement is an alcoholic drink, and the acid is an organic acid contained in the alcoholic drink.

6. An acidity measuring apparatus according to claim 1, wherein the subject for measurement is a serum treated by an enzyme, and the acid is a fatty acid freed by enzyme reaction of a lipid component in the serum.

7. An acidity measuring apparatus according to claim 1, wherein the reference electrode section includes a reference electrode which is formed of silver—silver chloride.

8. An acidity measuring apparatus according to claim 7, wherein the prescribed range is between +500 mV to −300 mV with respect to a potential of the reference electrode.

9. An acidity measuring apparatus according to claim 1, wherein the potential is swept within the prescribed range at a rate of 3 to 20 mV/second.

10. An acidity measuring apparatus according to claim 1, wherein the electrolyte is lithium perchloride soluble in an organic solvent.

11. An acidity measuring apparatus according to claim 1, wherein the counter electrode is formed of a corrosion-resistant conductive material.

12. An acidity measuring apparatus according to claim 11, wherein the corrosion-resistant conductive material is one of platinum, graphite, gold, stainless steel, aluminum, and an alloy thereof.

13. An acidity measuring apparatus according to claim 1, wherein an inner liquid in the reference electrode section is a solution containing one of silver chloride, potassium chloride, sodium chloride, lithium chloride, and copper sulfate.

14. An acidity measuring apparatus according to claim 1, wherein an inner liquid in the reference electrode section is a solution containing acetonitrile.

15. An acidity measuring apparatus according to claim 1, further comprising a salt bridge section for electrically connecting the electrode of the reference electrode section and the electrolyte solution, and the salt bridge section is formed of a porous ceramic material.

16. An acidity measuring apparatus according to claim 1, further comprising a salt bridge section for electrically connecting the electrode of the reference electrode section and the electrolyte solution, and the salt bridge section is formed of a porous glass material.

17. An acidity measuring apparatus according to claim 1, wherein the working electrode is formed of one of carbon and glassy carbon.

18. An acidity measuring apparatus according to claim 1, wherein the organic solvent is ethanol.

19. An acidity measuring apparatus according to claim 1, further comprising an acidity calculation device for calculating an acidity from th e pre-peak current value.

20. An acidity measuring apparatus, comprising:
    a measuring container, wherein the measuring container contains an electrolyte solution including one of a 1,2-benzoquinone derivative and a 1,4-benzoquinone derivative both having side chains on the benzene ring, an organic solvent, an electrolyte and an acid-containing subject for measurement;
    a working electrode, a counter electrode and a reference electrode section provided in the measuring container and immersed in the electrolyte solution; and
    a control section for sweeping a potential of the working electrode within a prescribed range and for detecting a value of a pre-peak current generated by the acid and flowing between the working electrode and the counter electrode, wherein the organic solvent is an ethanol-isooctane mixture solvent containing isooctane in the range of 35% to 70%.

21. An acidity measuring apparatus according to claim 20, wherein the 1,2-benzoquinone derivative has side chains at positions 3 and 5 of the benzene ring.

22. An acidity measuring apparatus according to claim 21, wherein the 1,2-benzoquinone derivative is 3,5-di-tert-butyl-1,2-benzoquinone.

23. An acidity measuring apparatus according to claim 20, wherein the 1,4-benzoquinone derivative has side chains at positions 2 and 6 of the benzene ring.

24. An acidity measuring apparatus according to claim 23, wherein the 1,4-benzoquinone derivative is 2,6-dimethyl-1,4-benzoquinone.

25. An acidity measuring apparatus, comprising:

a measuring container, wherein the measuring container contains an electrolyte solution including one of a 1,2-benzoquinone derivative and a 1,4-benzoquinone derivative both having side chains on the benzene ring, an organic solvent, an electrolyte and an acid-containing subject for measurement;

a working electrode, a counter electrode and a reference electrode section provided in the measuring container and immersed in the electrolyte solution; and a control section for sweeping a potential of the working electrode within a prescribed range and for detecting a value of a pre-peak current generated by the acid and flowing between the working electrode and the counter electrode, wherein the organic solvent is a mixture solvent is containing ethanol, water and isopropylalcohol.

26. A method for measuring an acidity of an acid-containing subject, comprising the steps of:

performing voltammetry of the electrolyte solution including the acid-containing subject for measurement; and performing a measurement to determine the value of a pre-peak current flowing in the electrolyte solution which appears at a potential which is positive with respect to a potential at which a peak of reduction of oxygen dissolved in the electrolyte solution, wherein the electrolyte solution includes one of a 1,2-benzoquinone derivative and a 1,4-benzoquinone derivative both having side chains on the benzene ring, where the 1,2-benzoquinone derivative is 3,5-di-tert-butyl-1,2-benzoquinone and the 1,4-benzoquinone derivative is 2,6-dimethyl-1,4-benzoquinone.

27. An acidity measuring apparatus, comprising:

a measuring container, wherein the measuring container contains an electrolyte solution including one of a 1,2-benzoquinone derivative and a 1,4-benzoquinone derivative both having side chains on the benzene ring, an organic solvent, an electrolyte and an acid-containing subject for measurement;

a working electrode, a counter electrode and a reference electrode section provided in the measuring container and immersed in the electrolyte solution; and a control section for sweeping a potential of the working electrode within a prescribed range and for detecting a value of a pre-peak current generated by the acid and flowing between the working electrode and the counter electrode, wherein the pre-peak current value has a positive potential with respect to a potential position at which appears the reduction current of oxygen dissolved in the electrolyte solution, and the 1,2-benzoquinone derivative is 3,5-di-tert-butyl-1,2-benzoquinone and the 1,4-benzoquinone derivative is 2,6-dimethyl-1,4-benzoquinone.

* * * * *